(12) United States Patent
Bose et al.

(10) Patent No.: US 12,223,400 B2
(45) Date of Patent: Feb. 11, 2025

(54) IMPACT MITIGATION AND PRESSURE MAPPING USING SMART FABRICS

(71) Applicant: INTERNATIONAL BUSINESS MACHINES CORPORATION, Armonk, NY (US)

(72) Inventors: Tathagato Bose, Kolkata (IN); Sourav Bhattacharjee, Durgapur (IN); Ranjeeth Pasupathi, Coimbatore (IN); Diwesh Pandey, Jeevan Bhima Nagar (IN)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 1030 days.

(21) Appl. No.: 17/249,076

(22) Filed: Feb. 19, 2021

(65) Prior Publication Data

US 2022/0269985 A1 Aug. 25, 2022

(51) Int. Cl.
*G06N 20/00* (2019.01)
*A41D 1/00* (2018.01)
(Continued)

(52) U.S. Cl.
CPC .......... *G06N 20/00* (2019.01); *A41D 1/002* (2013.01); *G06N 5/04* (2013.01); *G16H 10/60* (2018.01); *G16H 40/67* (2018.01); *G06N 3/08* (2013.01)

(58) Field of Classification Search
CPC . G06N 20/00; G06N 5/04; G06N 3/08; A41D 1/002; A41D 13/02; G16H 10/60;
(Continued)

(56) References Cited

U.S. PATENT DOCUMENTS

| 10,743,592 B2 | 8/2020 | Marikkar |
| 2005/0067816 A1* | 3/2005 | Buckman ............. A41D 13/018 280/730.1 |

(Continued)

OTHER PUBLICATIONS

Disclosed Anonymously, "Color-Changing "Smart Thread" Turns Fabric into a Computerized Display," UC Berkeley School of Information, Jun. 6, 2016 [accessed on Feb. 19, 2021], 7 pages, Retrieved from the Internet: <URL: https://www.ischool.berkeley.edu/news/2016/color-changing-smart-thread-turns-fabric-computerized-display>.

(Continued)

*Primary Examiner* — Etsub D Berhanu
*Assistant Examiner* — Joseph A Tombers
(74) *Attorney, Agent, or Firm* — Elliot J. Shine

(57) ABSTRACT

A method, computer system, and a computer program product for impact response is provided. The present invention may include triggering a stimulus if a threshold is reached or exceeded based on a positional relationship between a body suit and a single-track vehicle, wherein the stimulus activates one or more pressure sensors of the body suit. The present invention may include generating a pressure map of the body suit utilizing the one or more pressure sensors. The present invention may include generating an injury map using a machine learning model, wherein the injury map is based on the pressure map and one or more input parameters, and wherein the input parameters are specific to a user of the body suit.

19 Claims, 7 Drawing Sheets

(51) Int. Cl.
*G06N 3/08* (2023.01)
*G06N 5/04* (2023.01)
*G16H 10/60* (2018.01)
*G16H 40/67* (2018.01)

(58) Field of Classification Search
CPC .......... G16H 40/67; G16H 50/20; A61B 5/11; A61B 5/6804; A61B 5/7267
See application file for complete search history.

(56) References Cited

U.S. PATENT DOCUMENTS

| | | | | |
|---|---|---|---|---|
| 2012/0323501 | A1* | 12/2012 | Sarrafzadeh | G01L 1/18 702/41 |
| 2013/0317393 | A1* | 11/2013 | Weiss | A61B 5/447 600/587 |
| 2016/0143536 | A1 | 5/2016 | Hyde | |
| 2016/0379461 | A1 | 12/2016 | Gaidar | |
| 2017/0325520 | A1 | 11/2017 | Chu | |
| 2018/0153259 | A1 | 6/2018 | Iovu | |

OTHER PUBLICATIONS

Disclosed Anonymously, "Contextually Aware Clothing Variations," IP.com, Dec. 28, 2019, 6 pages, IP.com No. IPCOM000260862D, Retrieved from the Internet: <https://priorart.ip.com/IPCOM/000260862>.

Gomes, et al., "Development of pressure sensors for smart textiles," 18th World Textile Conference (AUTEX 2018), IOP Conference Series: Materials Science and Engineering, Jun. 2018, vol. 460, 20-22 , IOP Publishing Ltd., Istanbul, Turkey, DOI: 10.1088/1757-899X/460/1/012024, Retrieved from the Internet: <URL: https://iopscience.iop.org/article/10.1088/1757-899X/460/1/012024/pdf>.

Mell, et al., "The NIST Definition of Cloud Computing", National Institute of Standards and Technology, Special Publication 800-145, Sep. 2011, 7 pages.

Seth, "The Color of Pain," Yanko Design, Feb. 13, 2014 [accessed on Feb. 4, 2021], 6 pages, Retrieved from the Internet: <URL: https://www.yankodesign.com/2014/02/13/the-color-of-pain/>.

Yuen, et al., "Active Variable Stiffness Fibers for Multifunctional Robotic Fabrics," IEEE Robotics and Automation Letters, Jul. 2016 [accessed on Feb. 19, 2021], pp. 708-715, vol. 1, Issue 2, DOI: 10.1109/LRA.2016.2519609, Retrieved from the Internet: <URL: https://ieeexplore.ieee.org/document/7386608>.

* cited by examiner

IMPACT MITIGATION AND PRESSURE MAPPING USING SMART FABRICS

BACKGROUND

The present invention relates generally to the field of computing, and more particularly to smart fabrics.

Smart fabrics may be combined with natural fibers, which may enable the creation of clothing, such as, but not limited to body suits. Smart fabrics may be able to sense different environmental conditions as well as respond to stimuli. In response to certain stimuli, smart fabrics may be able to vary stiffness of the clothing. Varying stiffness of the clothing may be able to mitigate an impact of a fall on a user, such as, but not limited to, the impact between the user and a road or other surface. Smart fabrics may also be able to record data about an impact.

Data about an impact may be an important aspect of an emergency response if the user is unresponsive.

SUMMARY

Embodiments of the present invention disclose a method, computer system, and a computer program product for impact response. The present invention may include triggering a stimulus if a threshold is reached or exceeded based on a positional relationship between a body suit and a single-track vehicle, wherein the stimulus activates one or more pressure sensors of the body suit. The present invention may include generating a pressure map of the body suit utilizing the one or more pressure sensors. The present invention may include generating an injury map using a machine learning model, wherein the injury map is based on the pressure map and one or more input parameters, and wherein the input parameters are specific to a user of the body suit.

BRIEF DESCRIPTION OF THE SEVERAL VIEWS OF THE DRAWINGS

These and other objects, features and advantages of the present invention will become apparent from the following detailed description of illustrative embodiments thereof, which is to be read in connection with the accompanying drawings. The various features of the drawings are not to scale as the illustrations are for clarity in facilitating one skilled in the art in understanding the invention in conjunction with the detailed description. In the drawings.

DETAILED DESCRIPTION

Figure 1:
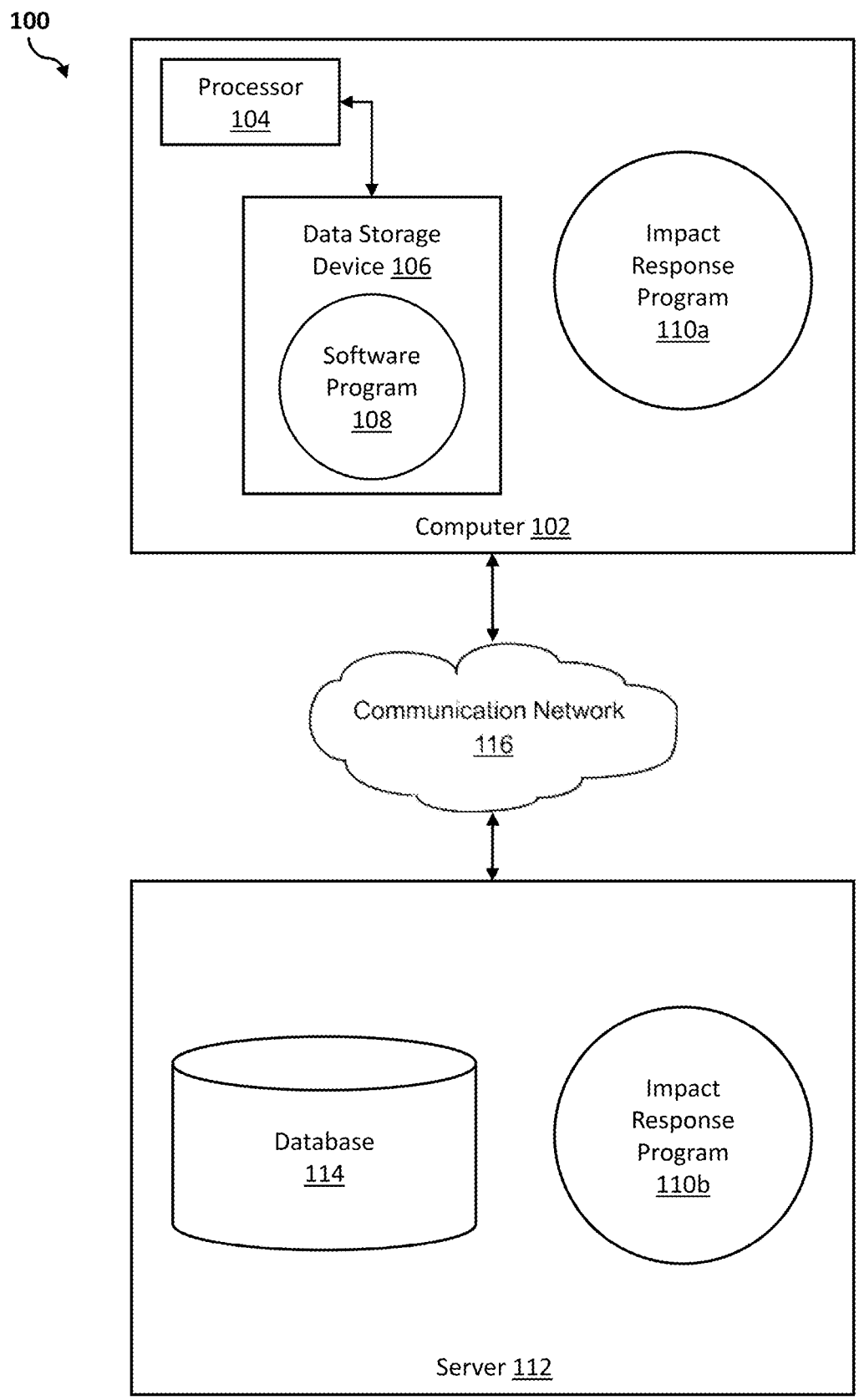
FIG. 1 illustrates a networked computer environment according to at least one embodiment.

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. Rather, these exemplary embodiments are provided so that this disclosure will be thorough and complete and will fully convey the scope of this invention to those skilled in the art. In the description, details of well-known features and techniques may be omitted to avoid unnecessarily obscuring the presented embodiments.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The following described exemplary embodiments provide a system, method and program product for impact response. As such, the present embodiment has the capacity to improve the technical field of smart fabrics by utilizing one or more pressure sensors of a body suit along with input parameters specific to a user display information about an impact. More specifically, the present invention may include triggering a stimulus if a threshold is reached or exceeded based on a positional relationship between a body suit and a single-track vehicle, wherein the stimulus activates one or more pressure sensors of the body suit. The present invention may include generating a pressure map of the body suit utilizing the one or more pressure sensors. The present invention may include generating an injury map using a machine learning model, wherein the injury map is based on the pressure map and one or more input parameters, and wherein the input parameters are specific to a user of the body suit.

As described previously, smart fabrics may be combined with natural fibers, which may enable the creation of clothing, such as, but not limited to body suits. Smart fabrics may be able to sense different environmental conditions as well as respond to stimuli. In response to certain stimuli, smart fabrics may be able to vary stiffness of the clothing. Varying stiffness of the clothing may be able to mitigate an impact of a fall on a user, such as, but not limited to, the impact between the user and a road or other surface. Smart fabrics may also be able to record data about an impact.

Data about an impact may be an important aspect of an emergency response if the user is unresponsive.

Therefore, it may be advantageous to, among other things, trigger a stimulus if a threshold is reached or exceeded based on a positional relationship between a body suit and a single-track vehicle, wherein the stimulus activates one or more pressure sensors of a body suit, generate a pressure map of the body suit utilizing the one or more pressure sensors, and generate an injury map using a machine learning model, wherein the injury map is based on the pressure map and one or more input parameters, and wherein the input parameters are specific to the user of the body suit.

According to at least one embodiment, the present invention may improve the ability of medical professionals to access an injury by displaying, using a body suit, a criticality level of an injury utilizing one or more colors.

According to at least one embodiment, the present invention may improve the utilization of smart fabric in displaying impact (e.g., applied pressure) triggering a stimulus if a threshold is reached or exceeded based on a positional relationship between a body suit and a single-track vehicle, wherein the stimulus activates one or more pressure sensors of the body suit. The present invention may utilize an electric current to trigger the stimulus. The stimulus may stiffen the smart fibers of the body suit by interacting with the shape memory alloy, such as, nickel-titanium alloy, and the thermally responsive polymers, such as, thermoplastic, which may adapt the body suit for impact.

According to at least one embodiment, the present invention may improve user safety by utilizing the smart fabric of a body suit to mitigate the impact of a fall on a user by using an electric stimulus to stiffen the upper and lower layer of the body suit. The electric stimulus may also stiffen a third layer, the third layer being designed in a wave like structure to enable air between the waves to further mitigate the impact of the fall on the user.

According to at least one embodiment, the present invention may improve the safety of single-track vehicles by using a kinetics monitor installed in the single-track vehicle and data being received from the body suit to monitor a positional relationship between the single-track vehicle and the user of the body suit. The electric stimulus being triggered to protect the user of the body suit based on one or more parameters between the user of the body suit and the single-track vehicle.

According to at least one embodiment, the present invention may improve the mapping of impact by utilizing neighborhood pressure expansion. Neighborhood pressure expansion being the expansion of a pressure region to one or more surrounding pixels of the pressure map based on one or more input parameters. The input parameters may be specific to the user and may include, but are not limited to including, age of the user, gender of the user, biological parameters of the user, medical history of the user, body structure of the user, amongst others. The present invention may utilize these input parameters to expand the pressure regions.

According to at least one embodiment, the present invention may improve the mapping of impact by determining a pressure mapping correlation. The pressure mapping correlation may be a correlation between two or more body parts of the user based on the one or more input parameters.

According to at least one embodiment, the present invention may improve pressure mapping and injury mapping by utilizing a trained machine learning model to generate an injury map based on the pressure map and one or more input parameters.

According to at least one embodiment, the present invention may improve body suits utilizing smart fabric by using a scannable portion to allow a medical professional to gather information on an unresponsive user of the body suit.

Referring to FIG. 1, an exemplary networked computer environment 100 in accordance with one embodiment is depicted. The networked computer environment 100 may include a computer 102 with a processor 104 and a data storage device 106 that is enabled to run a software program 108 and an impact response program 110a. The networked computer environment 100 may also include a server 112 that is enabled to run an impact response program 110b that may interact with a database 114 and a communication network 116. The networked computer environment 100 may include a plurality of computers 102 and servers 112, only one of which is shown. The communication network 116 may include various types of communication networks, such as a wide area network (WAN), local area network (LAN), a telecommunication network, a wireless network, a public switched network and/or a satellite network. It should be appreciated that FIG. 1 provides only an illustration of one implementation and does not imply any limitations with regard to the environments in which different embodiments may be implemented. Many modifications to the depicted environments may be made based on design and implementation requirements.

The client computer 102 may communicate with the server computer 112 via the communications network 116. The communications network 116 may include connections, such as wire, wireless communication links, or fiber optic cables. As will be discussed with reference to FIG. 5, server computer 112 may include internal components 902a and external components 904a, respectively, and client computer 102 may include internal components 902b and external components 904b, respectively. Server computer 112 may also operate in a cloud computing service model, such as Software as a Service (SaaS), Platform as a Service (PaaS), or Infrastructure as a Service (IaaS). Server 112 may also be located in a cloud computing deployment model, such as a private cloud, community cloud, public cloud, or hybrid cloud. Client computer 102 may be, for example, a mobile device, a telephone, a personal digital assistant, a netbook, a laptop computer, a tablet computer, a desktop computer, or any type of computing devices capable of running a program, accessing a network, and accessing a database 114. According to various implementations of the present embodiment, the impact response program 110a, 110b may interact with a database 114 that may be embedded in various storage devices, such as, but not limited to a computer/mobile device 102, a networked server 112, or a cloud storage service.

According to the present embodiment, a user using a client computer 102 or a server computer 112 may use the impact response program 110a, 110b (respectively) to trigger a stimulus based on a threshold, wherein the stimulus activates one or more pressure sensors of a body suit, generate a pressure map of the body suit utilizing the one or more pressure sensors, and generate an injury map using a machine learning model, wherein the injury map is based on the pressure map and one or more input parameters, and wherein the input parameters are specific to the user of the body suit. The impact response method is explained in more detail below with respect to FIGS. 2, 3, and 4 below.

Figure 2:
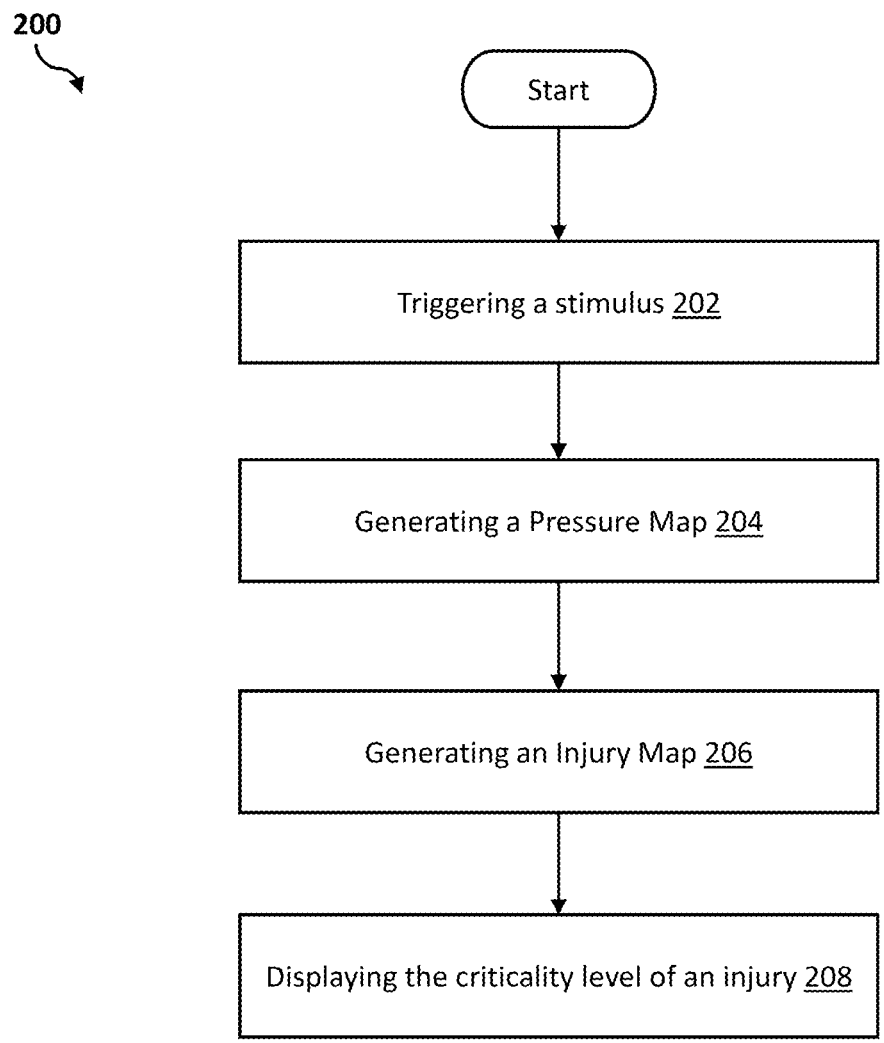
FIG. 2 is an operational flowchart illustrating a process for impact response according to at least one embodiment.

Referring now to FIG. 2, an operational flowchart illustrating the exemplary impact response process 200 used by the impact response program 110a and 110b (hereinafter impact response program 110) according to at least one embodiment is depicted.

At 202, the impact response program triggers a stimulus. The impact response program 110 may trigger a stimulus in a body suit. The body suit may be comprised of smart fabric. Smart fabrics (e.g., smart textiles, electronic textiles, e-textiles, smart garments, smart threads, intelligent textiles, smart fibers) may be able to sense environmental changes, and may be able to respond to surroundings or stimuli, such as, but not limited to, electrical fields, heat, and movement. Smart fabrics may interact with the body of a user and may sense the user's physiology and structure. The body suit may be comprised of smart fabric having a variable stiffness and thermally responsive polymers.

The body suit may be comprised of three layers, an outer layer, an inner layer, and a third layer between the inner and outer layer. The third layer may be in the shape of waves in between the former mentioned upper and lower layer. The electric stimulus may stiffen the upper and lower layers. The electric stimulus may stiffen the wave-like structure of of the third layer which may create an air gap between the outer and inner layer between the waves of the third layer.

The impact response program 110 may trigger the stimulus when the threshold is reached or exceeded. The impact response program 110 may utilize an electric current to trigger the stimulus. The stimulus may stiffen the smart fabric of the body suit by interacting with a shape memory alloy, such as, nickel-titanium alloy, and the thermally responsive polymers, such as, thermoplastic, which may adapt the body suit for impact and may mitigate injury of the user. The impact response program 110 may also activate one or more pressure sensors, as will be explained in more detail below with respect to step 204, the impact response program 110 may utilize the one or more pressure sensors to generate a pressure map.

The impact response program 110 may determine the threshold is reached or exceeded based on a positional relationship between the user and a single-track vehicle. The impact response program 110 may monitor the positional relationship between the user and the single-track vehicle by utilizing the body suit to monitor the position of the user and a kinematics monitor attached to the single-track vehicle to monitor the position of the single-track vehicle. The threshold may be a predetermined value that if reached or exceeded may correlate to a point in which the user has irreversibly lost controllable operation of the single-track vehicle. The single-track vehicle may be a vehicle that leaves a single ground track as it moves forward. The single-track vehicle may have less lateral stability than other vehicles. Single-track vehicles may include, but are not limited to including, bicycles, tandem bicycles, motorcycles, scooters, dirt bikes, mopeds, unicycles, amongst others.

The impact response program 110 may utilize one or more parameters in monitoring the positional relationship between the between the user and the single-track vehicle and determining whether the threshold is reached or exceeded. The one or more parameters utilized by the impact response program 110 may include, but are not limited to including, coefficient of friction of a surface or road, velocity of a single-track vehicle, radius of curvature of the surface or road, relative velocity of air, direction of air, air friction, inclination angle, composite center of gravity, moving center of gravity, amongst others. For example, the impact response program 110 may utilize the kinematics monitor attached to the single-track vehicle in conjunction with the body suit to monitor the composite center of gravity of both the user and the single-track vehicle to determine the composite center of gravity, the composite center of gravity being the center of gravity relationship between the user and the single-track vehicle.

The impact response program 110 may additionally utilize one or more laws of physics, such as, but not limited to, Newton's laws of motion. The impact response program 110 may also consider properties of the single-track vehicle, such as, but not limited to, understeer, oversteer, yaw motion, curvature response, lateral acceleration, amongst others.

In determining whether the positional relationship between the user and the single-track vehicle reaches or exceeds the threshold, the impact response program 110 may use the following equations:

$$\mu mg = mg \cos\theta$$

$$\frac{mv^2}{r} = mg \sin\theta$$

The axial values utilized for direction are the x axis, y axis, and z axis. The x axis may represent the gravitational force, the y axis may represent the width of a road or surface, and the z axis may represent the single-track vehicle moving towards this axis. In the above equations, $\mu mg$ may be frictional force, $\theta$ may be the inclination angle of the single-track vehicle, m may be the composite mass of the single-track vehicle and the user at center of gravity, v may be the velocity of the single-track vehicle, r may be the radius of curvature of the road or surface, $$\frac{mv^2}{r}$$

may be the centrifugal force, and $\mu$ may be the coefficient of friction. Frictional force $\mu mg$ may be balanced by $mg \cos\theta$ and centrifugal force $$\frac{mv^2}{r}$$

may be balanced $mg \sin\theta$.

The impact response program 110 may also consider the influence of air friction in the equations above. The $v_{air}^{rel}$ may work along the z axis, and $v_{air}^{rel} \sin\theta$ may be added to $mg \cos\theta$ and $v_{air}^{rel} \cos\theta$ may be added to $$\frac{mv^2}{r}.$$

For example, the user of the body suit comprised of smart fabric may be riding a single-track vehicle, such as a motor cycle. The impact response program 110 may utilize the kinetics monitor installed on the motor cycle as well as the information being received from the body suit of the user determine the one or more parameters such as velocity, center of gravity, and inclination angle. The impact response program 110 may utilize the one or more parameters in monitoring the positional relationship between the user and the single-track vehicle and determining whether the threshold is reached or exceeded. If the user loses control of the motor cycle such that falling becomes the only available option the impact response program 110 may determine the threshold has been reached or exceeded at which time the impact response program 110 may utilize the electric current to trigger the stimulus within the body suit worn by the user. The stimulus may stiffen the smart fabric of the body suit to mitigate the impact between the user and a road or other surface, which may reduce or eliminate injuries to the user. The impact response program 110 may also activate one or more pressure sensors integrated into the smart fabric of the body suit when the threshold is reached or exceeded. As will be explained in more detail below with respect to step 204, the impact response program 110 may utilize the one or more pressure sensors to generate a pressure map.

At 204, the impact response program generates a pressure map. The impact response program 110 may generate the pressure map based on impact. The impact response program 110 may utilize one or more pressure sensors integrated into the smart fabric to generate the pressure map. The one or more pressure sensors integrated into the smart fabric may be utilized to measure the impact (e.g., applied pressure) to the body suit.

The one or more pressure sensors may be integrated into the smart fabric of the body suit using one or more piezoresistive materials. Piezoresistive materials may be a metal or semiconductor in which an electrical resistance varies in response to applied pressure (e.g., impact). Piezoresistive materials may include, but are not limited to including, germanium, polycrystalline silicon, amorphous silicon, silicon carbide, single crystal silicon, amongst others. The impact response program 110 may determine the impact (e.g., applied pressure) to the body suit using a voltage difference based on the electrical resistance variation. The impact response program 110 may utilize a micro-controller to measure the electrical resistance as a function of time which may record the highest pressure applied to a specific portion of the body suit.

The pressure map may be a bitmap (e.g., bit array, bitmap index), the bitmap being comprised of a plurality of pixels. The plurality of pixels having a value representing the impact or pressure applied to that area. Each pixel may have a corresponding intersection point, the corresponding intersection point may be the intersecting points of the smart fabric of the body suit. The intersecting points of the smart fabric may represent a corresponding spot on the body suit and therefore a body part of the user. The value representing the impact or pressure may be normalized between 0 and 1, wherein 0 represents no contact and 1 represents direct impact.

The impact response program 110 may generate the pressure map for a cross section of the smart fabric. The smart fabric may be a curved surface and the intersecting points of the curved surface may be located with values, such as D, x, y, z, values. The impact response program may take a two dimensional (2D) cross section of the curved surface to generate the pressure map for the cross section of the smart fabric, where the cross section may correspond to a part of the body of the user. The pressure map may utilize the location vector (e.g., D, x, y, z) to train a machine learning model for all users.

At 206, the impact response program generates an injury map. The impact response program 110 may generate the injury map based on the pressure map and a machine learning model. The machine learning model may be trained using one or more input parameters, such as, but not limited to, age of the user, gender of the user, biological parameters of the user, medical history of the user, body structure of the user, amongst others. The impact response program 110 may store the one or more input parameters received from the user in a centralized database 114 (e.g., database 114). The machine learning model may be trained using the one or more input parameters received from a plurality of users and a plurality of body suits.

The impact response program 110 may utilize a deep neural network (DNN) as the machine learning model. A DNN may be an artificial neural network (ANN) with multiple layers between the input and output layers. The DNN may be trained using one or more input parameters. The DNN may utilize the one or more input parameters of the user to determine the neighborhood pressure expansion. The DNN may utilize the one or more input parameters of the user to determine the pressure mapping correlation.

The machine learning model may utilize the one or more input parameters to determine a neighborhood pressure expansion. The neighborhood pressure expansion may be utilized to expand a pressure region to surrounding pixels based on the impact or pressure of an intersecting point to one or more surrounding pixels based on the one or more input parameters. For example, the machine learning model may expand the pressure mapping to one or more pixels around the pixel corresponding to an intersection point with a direct impact based on the age of the user. The neighborhood pressure expansion will be described in more detail with respect to FIG. 3 below.

The machine learning model may utilize the one or more parameters to determine a pressure mapping correlation. The pressure mapping correlation may be the correlation between two or more body parts based on the one or more input parameters. For example, the machine learning model may determine based on the user's medical history that based on a prior injury to the elbow an impact to the fabric cross section of the body suit corresponding to the shoulder may have a greater impact on the elbow. The pressure mapping correlation will be described in more detail below with respect to FIG. 4.

The impact response program may generate the injury map for the user by utilizing the pressure map and the machine learning model. The impact response program 110 utilize the pressure map using the neighborhood pressure expansion and the pressure mapping correlation determined using the machine learning model to generate the injury map for the user.

At 208, the impact response program displays a criticality level of an injury. The criticality level may be determined based on the injury map. The criticality of the injury may represent the severity of the injury to one or more body parts of the user. The impact response program 110 may display, using the body suit, the criticality level of an injury to the user utilizing one or more colors. The one or more colors may have a corresponding criticality level.

The impact response program 110 may utilize the intersecting points of the injury map and their values to color code the body suit. The impact response program 110 may utilize different colors to indicate the criticality level of the injury. For example, the impact response program may utilize darker colors to indicate areas of the body suit where the criticality level of the injury is higher.

The impact response program 110 may display the criticality level of the injury by displaying the injury map. The impact response program 110 may utilize the injury map and the values for each of the intersecting points of the injury map to display the criticality level of the injury. The impact response program 110 may translate the injury map into one or more injury captions. The one or more injury captions may describe the injury map in words. Injury captions may include, but are not limited to including, bruise, scratch, external deep wound, internal injury, amongst others. The impact response program 110 may display a corresponding body part of the user with the one or more injury captions. For example, external deep wound—shoulder, or internal injury—lungs.

The impact response program 110 may also display the one or more input parameters as well as information about the impact. The body suit may have a scannable portion, such as, but not limited to a barcode, storing the one or more input parameters of the user. The scannable portion also may include information about the impact, such as, but not limited to, the velocity of the user at the time of the accident, time of impact, amongst other information. The impact response program 110 may utilize the scannable portion to display the criticality level of the injury.

The impact response program 110 may utilize the injury map to generate an injury caption. The injury caption being a text analysis of the injury map. The injury response program may determine based on the injury map whether an area was bruised or scratched, has a deep external wound, or an internal injury.

The impact response program 110 may receive feedback on the accuracy of the injury map. The impact response program 110 may retrain the machine learning model based on the feedback received on the accuracy of the injury map. The machine learning model may utilize feedback to learn detailed injury descriptions.

For example, the user may be unresponsive, and a medical professional or first responder may utilize the injury map to determine the criticality of various injuries. The first responder may determine the accuracy of the injury map and provide feedback to retrain the machine learning model.

The machine learning model may utilize one or more diagnosis of the injury to determine injuries in the future. For example, the impact response program 110 may receive feedback that the impact resulted in a broken rib. The impact response program 110 may train the machine learning model based on the one or more user parameters and information about the impact, such as, but not limited to, velocity of the user at the time of impact to further improve injury captioning.

Figure 3:
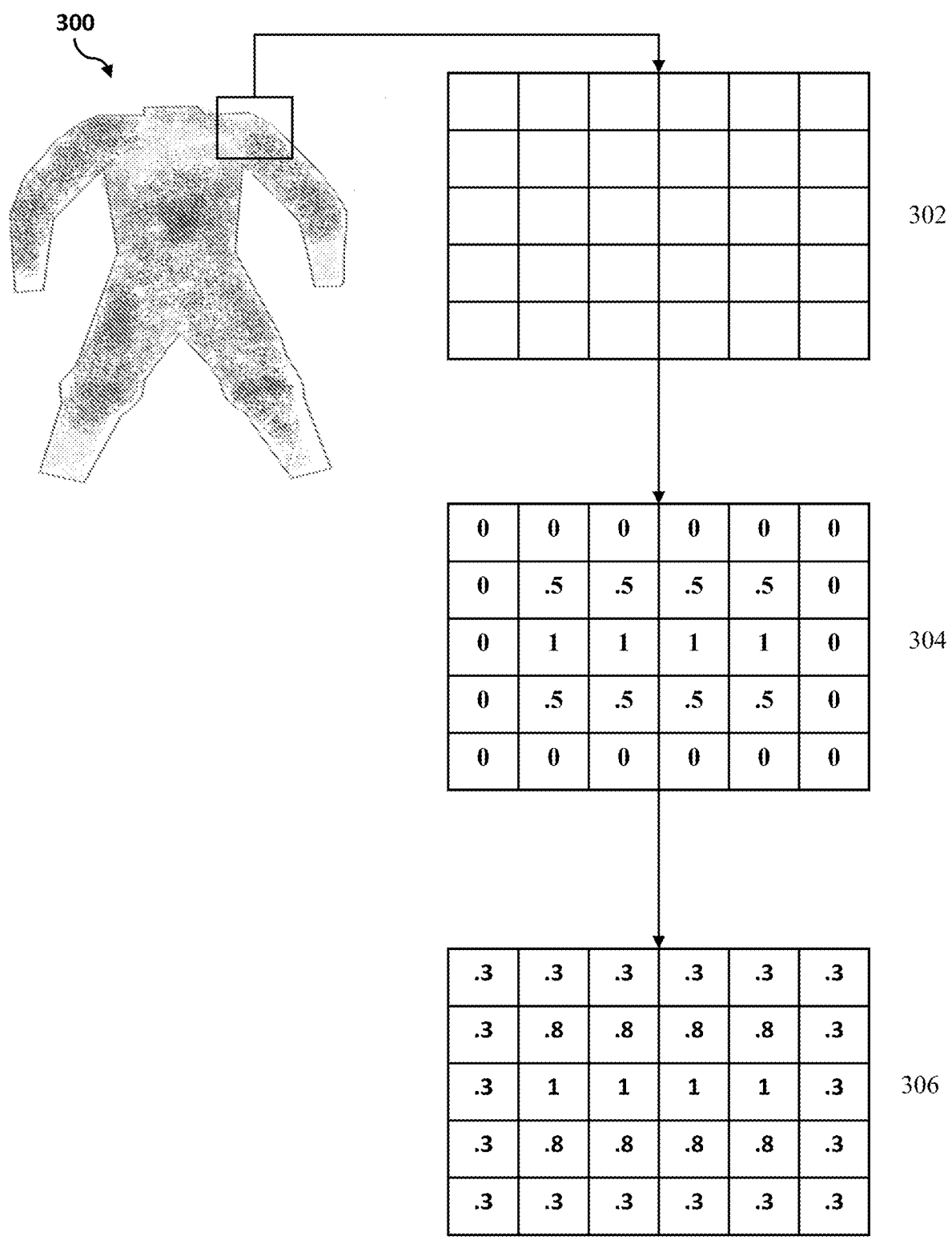
FIG. 3 is an operational flowchart illustrating a process for neighborhood pressure expansion according to at least one embodiment.

Referring now to FIG. 3, an operational flowchart illustrating the exemplary neighborhood pressure expansion process 300 used by the impact response program 110 according to at least one embodiment is depicted. The neighborhood pressure expansion process 300 of FIG. 3 is substantially similar to the impact response process 200 of FIG. 2 with steps 302-306 being added between steps 206 and 208.

At 302 the impact response program determines a fabric cross section corresponding to a particular body part of the user. The intersecting points in the smart fabric may be represented by a corresponding pixel which has a value between 0 and 1 representing the impact or pressure applied to that body part of the user.

At 304 the impact response program generates a pressure map based on the impact or pressure applied to that body part of the user. The impact response program 110 may utilize pressure sensors within the body suit to generate the pressure map based on the impact or pressure applied to that body part of the user.

At 306 the impact response program determines the neighborhood pressure expansion. The impact response program 110 may determine the neighborhood pressure expansion by utilizing the pressure map generated in step 302 and applying the one or more input parameters of the user.

The one or more input parameters utilized to determine the neighborhood pressure expansion may include, but are not limited to including, the age and gender of the user. The impact response program 110 may utilize a trained machine learning model to determine the neighborhood pressure expansion. The neighborhood pressure expansion may be an updated pressure map with an expanded pressure region corresponding to the age and gender of the user.

For example, if an 80 year old individual were to fall off a single-track vehicle while wearing the body suit the one or more pressure sensors may generate the pressure map depicted at 304, however, the impact response program 110 may determine based on the neighborhood pressure expansion a more accurate pressure map may be the pressure map illustrated at 306.

Figure 4:
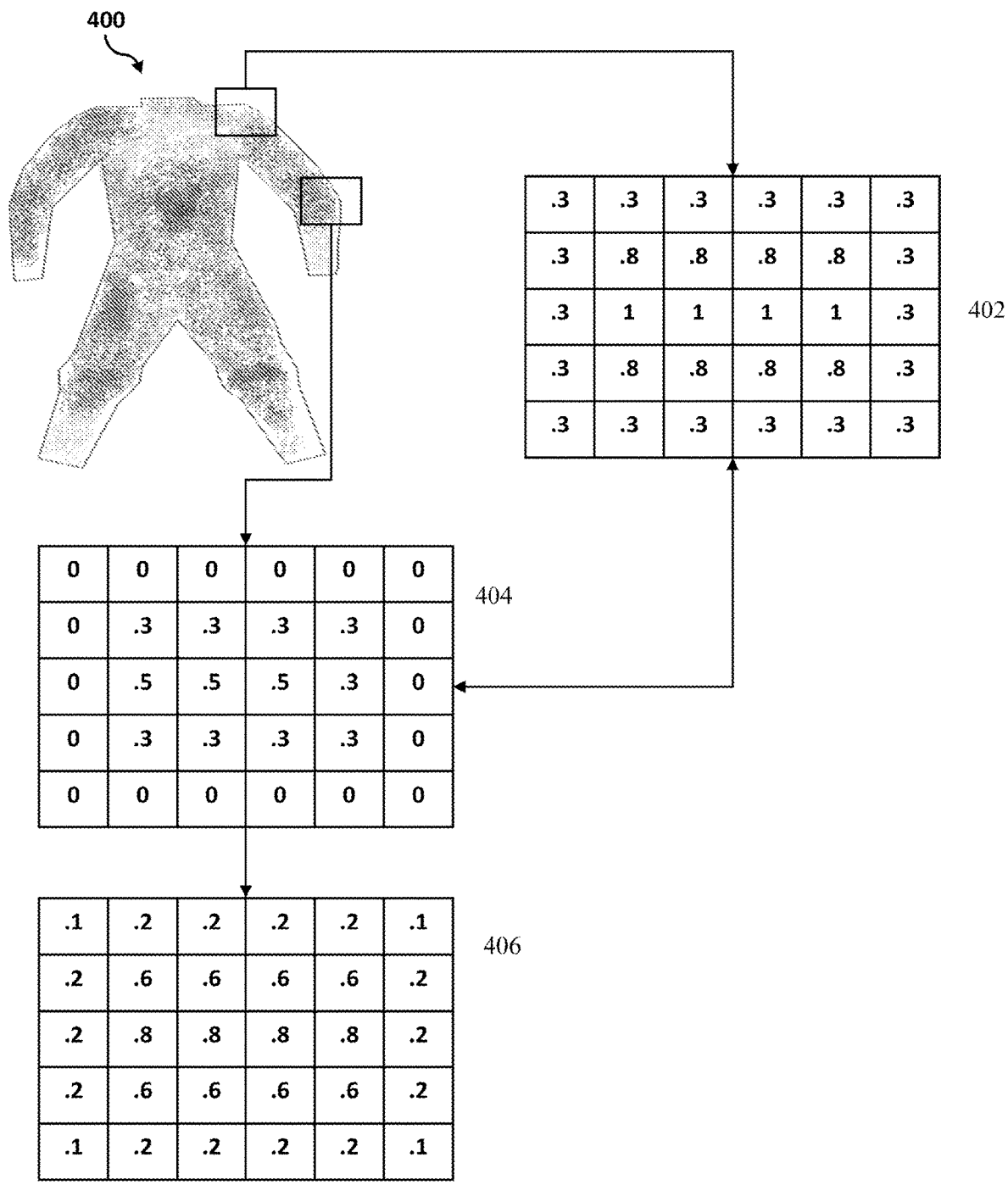
FIG. 4 is an operational flowchart illustrating a process for pressure mapping correlation according to at least one embodiment.

Referring now to FIG. 4, an operational flowchart illustrating the exemplary pressure mapping correlation process 400 used by the impact response program 110 according to at least one embodiment is depicted. The pressure mapping correlation process 400 of FIG. 4 is substantially similar to the impact response process 200 of FIG. 2 with steps 402-406 being added between steps 206 and 208.

At 402 the impact response program determines the pressure mapping correlation. The pressure mapping correlation may be the correlation between two or more body parts of the user based on the one or more input parameters.

The one or more input parameters utilized to determine the pressure mapping correlation may include, but are not limited to including, age of the user, gender of the user, biological parameters of the user, medical history of the user, body structure of the user, amongst others.

Input parameters such as, but not limited to, the body structure of the user may be determined by the impact response program 110 based on the dimensions of the body suit. The one or more input parameters may also be provided by the user.

The pressure map depicted at 402 may correspond to the pressure map with the expanded pressure region from step 306. The pressure map depicted at 402 may correspond to the shoulder region of the user.

At 404, the impact response program determines two or more correlated body parts. Here, the pressure map for the shoulder of the user is depicted by 402 and the pressure map for the elbow of the user is depicted by 404.

At 406, the impact response program generates an injury map. The impact response program may generate the injury map for the elbow if the user, depicted by 406, by utilizing the one or more input parameters.

For example, the machine learning model may determine based on users with similar medical history and age, the impact or pressure to the shoulder of the user may alter the pressure map for the elbow depicted in 404 to result in the injury map 406.

It may be appreciated that FIGS. 2, 3, and 4 provide only an illustration of one embodiment and do not imply any limitations with regard to how different embodiments may be implemented. Many modifications to the depicted embodiment(s) may be made based on design and implementation requirements.

Figure 5:
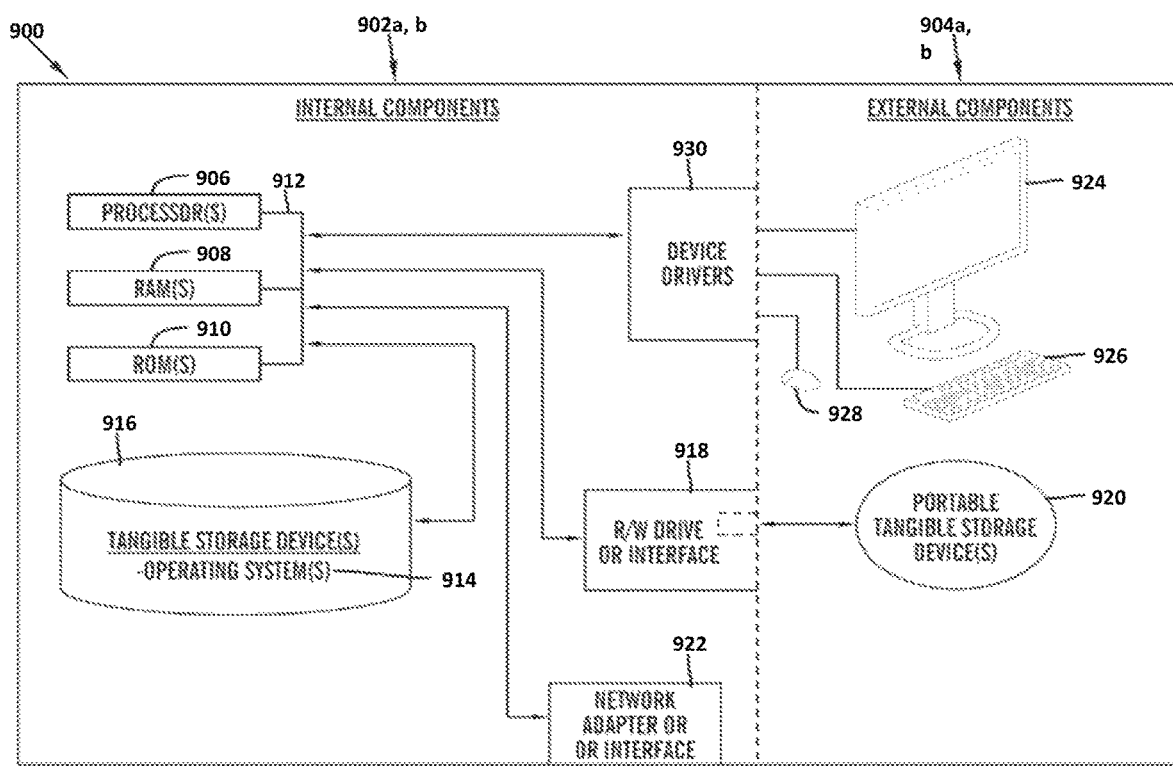
FIG. 5 is a block diagram of internal and external components of computers and servers depicted in FIG. 1 according to at least one embodiment.

FIG. 5 is a block diagram 900 of internal and external components of computers depicted in FIG. 1 in accordance with an illustrative embodiment of the present invention. It should be appreciated that FIG. 5 provides only an illustration of one implementation and does not imply any limitations with regard to the environments in which different embodiments may be implemented. Many modifications to the depicted environments may be made based on design and implementation Data processing system 902, 904 is representative of any electronic device capable of executing machine-readable program instructions. Data processing system 902, 904 may be representative of a smart phone, a computer system, PDA, or other electronic devices. Examples of computing systems, environments, and/or configurations that may be represented by data processing system 902, 904 include, but are not limited to, personal computer systems, server computer systems, thin clients, thick clients, hand-held or laptop devices, multiprocessor systems, microprocessor-based systems, network PCs, minicomputer systems, and distributed cloud computing environments that include any of the above systems or devices.

User client computer 102 and network server 112 may include respective sets of internal components 902a, b and external components 904a, b illustrated in FIG. 5. Each of the sets of internal components 902a, b includes one or more processors 906, one or more computer-readable RAMs 908 and one or more computer-readable ROMs 910 on one or more buses 912, and one or more operating systems 914 and one or more computer-readable tangible storage devices 916. The one or more operating systems 914, the software program 108, and the impact response program 110a in client computer 102, and the impact response program 110b in network server 112, may be stored on one or more computer-readable tangible storage devices 916 for execution by one or more processors 906 via one or more RAMs 908 (which typically include cache memory). In the embodiment illustrated in FIG. 5, each of the computer-readable tangible storage devices 916 is a magnetic disk storage device of an internal hard drive. Alternatively, each of the computer-readable tangible storage devices 916 is a semiconductor storage device such as ROM 910, EPROM, flash memory or any other computer-readable tangible storage device that can store a computer program and digital information.

Each set of internal components 902a, b also includes a R/W drive or interface 918 to read from and write to one or more portable computer-readable tangible storage devices 920 such as a CD-ROM, DVD, memory stick, magnetic tape, magnetic disk, optical disk or semiconductor storage device. A software program, such as the software program 108 and the impact response program 110a and 110b can be stored on one or more of the respective portable computer-readable tangible storage devices 920, read via the respective R/W drive or interface 918 and loaded into the respective hard drive 916.

Each set of internal components 902a, b may also include network adapters (or switch port cards) or interfaces 922 such as a TCP/IP adapter cards, wireless wi-fi interface cards, or 3G or 4G wireless interface cards or other wired or wireless communication links. The software program 108 and the impact response program 110a in client computer 102 and the impact response program 110b in network server computer 112 can be downloaded from an external computer (e.g., server) via a network (for example, the Internet, a local area network or other, wide area network) and respective network adapters or interfaces 922. From the network adapters (or switch port adaptors) or interfaces 922, the software program 108 and the impact response program 110a in client computer 102 and the impact response program 110b in network server computer 112 are loaded into the respective hard drive 916. The network may comprise copper wires, optical fibers, wireless transmission, routers, firewalls, switches, gateway computers and/or edge servers.

Each of the sets of external components 904a, b can include a computer display monitor 924, a keyboard 926, and a computer mouse 928. External components 904a, b can also include touch screens, virtual keyboards, touch pads, pointing devices, and other human interface devices. Each of the sets of internal components 902a, b also includes device drivers 930 to interface to computer display monitor 924, keyboard 926 and computer mouse 928. The device drivers 930, R/W drive or interface 918 and network adapter or interface 922 comprise hardware and software (stored in storage device 916 and/or ROM 910).

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 6:
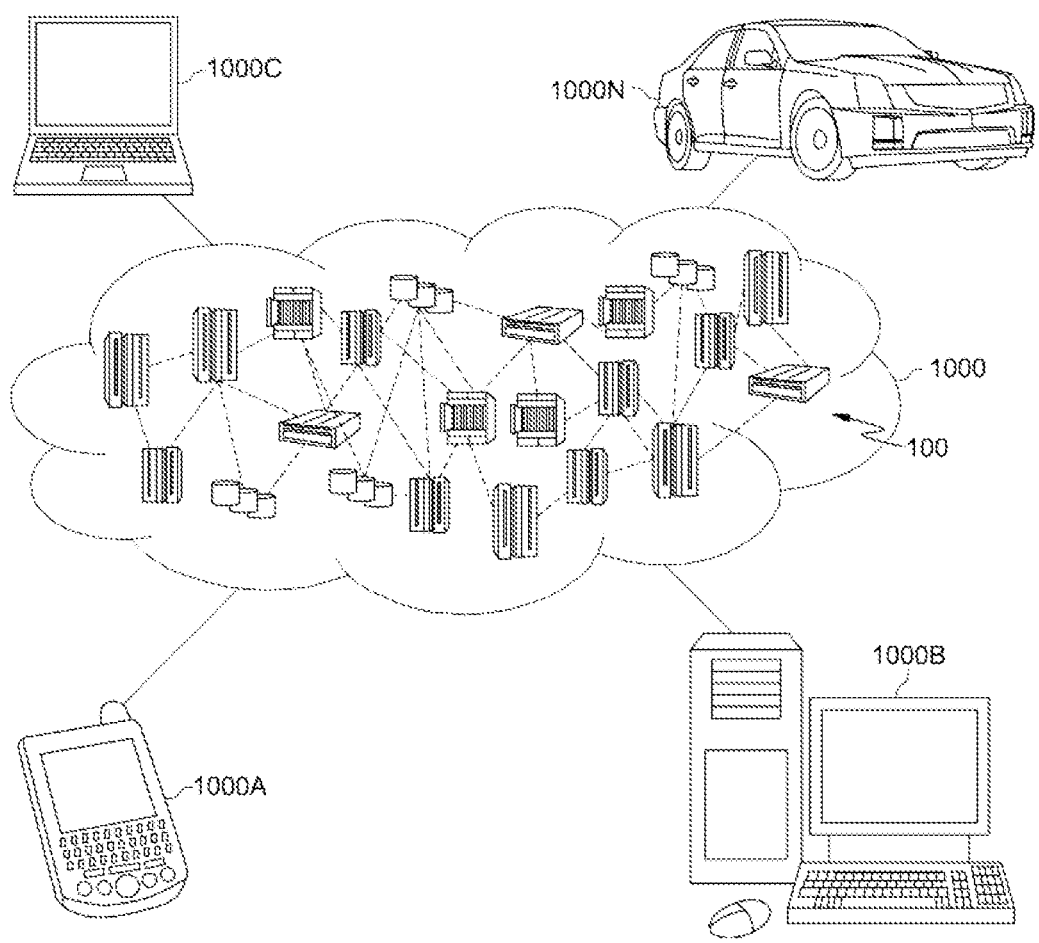
FIG. 6 is a block diagram of an illustrative cloud computing environment including the computer system depicted in FIG. 1, in accordance with an embodiment of the present disclosure.

Referring now to FIG. 6, illustrative cloud computing environment 1000 is depicted. As shown, cloud computing environment 1000 comprises one or more cloud computing nodes 100 with which local computing devices used by cloud consumers, such as, for example, personal digital assistant (PDA) or cellular telephone 1000A, desktop computer 1000B, laptop computer 1000C, and/or automobile computer system 1000N may communicate. Nodes 100 may communicate with one another. They may be grouped (not shown) physically or virtually, in one or more networks, such as Private, Community, Public, or Hybrid clouds as described hereinabove, or a combination thereof. This allows cloud computing environment 1000 to offer infrastructure, platforms and/or software as services for which a cloud consumer does not need to maintain resources on a local computing device. It is understood that the types of computing devices 1000A-N shown in FIG. 6 are intended to be illustrative only and that computing nodes 100 and cloud computing environment 1000 can communicate with any type of computerized device over any type of network and/or network addressable connection (e.g., using a web browser).

Figure 7:
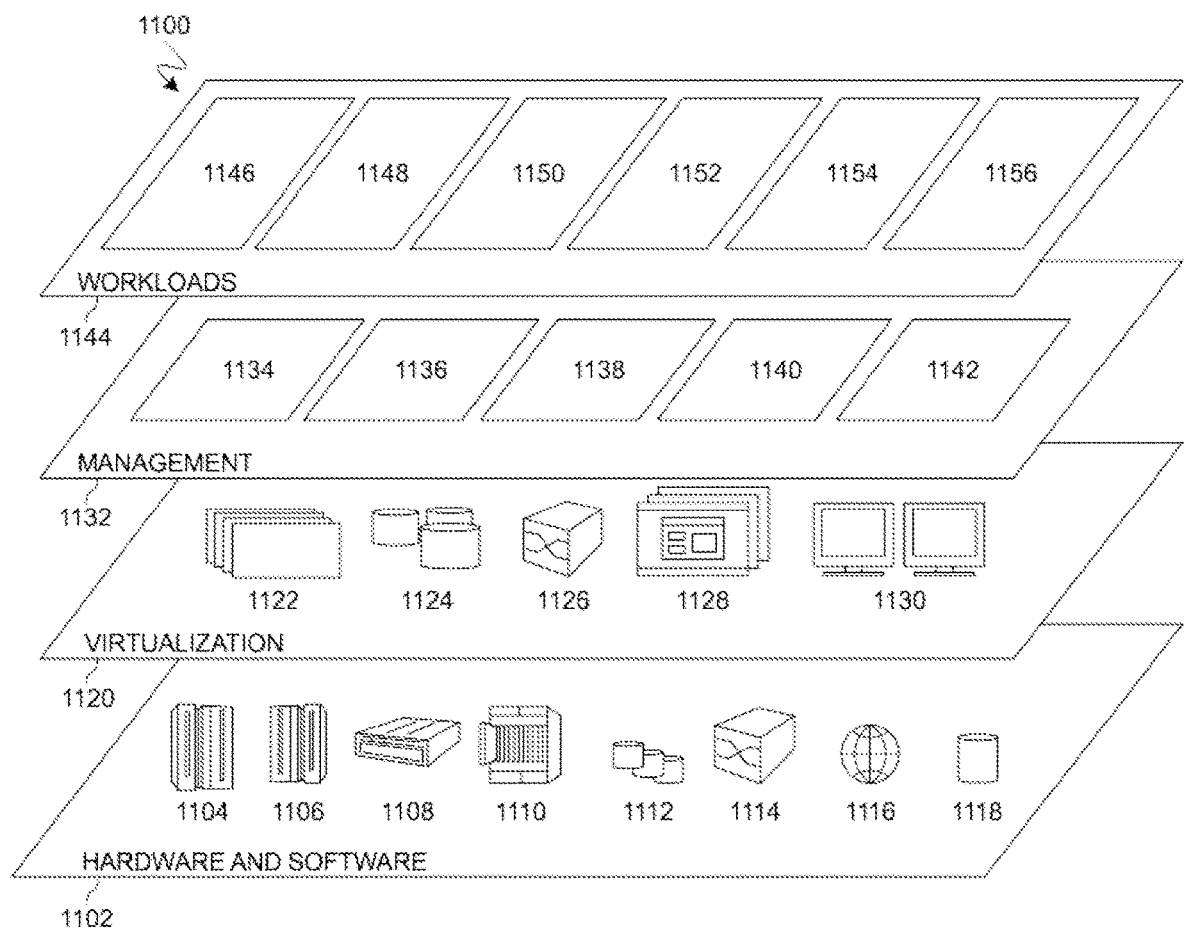
FIG. 7 is a block diagram of functional layers of the illustrative cloud computing environment of FIG. 6, in accordance with an embodiment of the present disclosure.

Referring now to FIG. 7, a set of functional abstraction layers 1100 provided by cloud computing environment 1000 is shown. It should be understood in advance that the components, layers, and functions shown in FIG. 7 are intended to be illustrative only and embodiments of the invention are not limited thereto. As depicted, the following layers and corresponding functions are provided:

Hardware and software layer 1102 includes hardware and software components. Examples of hardware components include: mainframes 1104; RISC (Reduced Instruction Set Computer) architecture based servers 1106; servers 1108; blade servers 1110; storage devices 1112; and networks and networking components 1114. In some embodiments, software components include network application server software 1116 and database software 1118.

Virtualization layer 1120 provides an abstraction layer from which the following examples of virtual entities may be provided: virtual servers 1122; virtual storage 1124; virtual networks 1126, including virtual private networks; virtual applications and operating systems 1128; and virtual clients 1130.

In one example, management layer 1132 may provide the functions described below. Resource provisioning 1134 provides dynamic procurement of computing resources and other resources that are utilized to perform tasks within the cloud computing environment. Metering and Pricing 1136 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 1138 provides access to the cloud computing environment for consumers and system administrators. Service level management 1140 provides cloud computing resource allocation and management such that required service levels are met. Service Level Agreement (SLA) planning and fulfillment 1142 provide pre-arrangement for, and procurement of, cloud computing resources for which a future requirement is anticipated in accordance with an SLA.

Workloads layer 1144 provides examples of functionality for which the cloud computing environment may be utilized. Examples of workloads and functions which may be provided from this layer include: mapping and navigation 1146; software development and lifecycle management 1148; virtual classroom education delivery 1150; data analytics processing 1152; transaction processing 1154; and impact response 1156. An impact response program 110a, 110b provides a way to trigger a stimulus based on a threshold, wherein the stimulus activates one or more pressure sensors of a body suit, generate a pressure map of the body suit utilizing the one or more pressure sensors, and generate an injury map using a machine learning model, wherein the injury map is based on the pressure map and one or more input parameters, and wherein the input parameters are specific to the user of the body suit.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for impact response, the method comprising:
triggering a stimulus if a threshold is reached or exceeded based on a positional relationship between a user of a body suit and a single-track vehicle, wherein the stimulus activates one or more pressure sensors integrated into a smart fabric of the body suit designed to measure an impact to the body suit;
generating a pressure map of the body suit utilizing the one or more pressure sensors, wherein the pressure map is comprised of a plurality of pixels corresponding to a plurality of intersection points of the smart fabric of the body suit, wherein each of the plurality of pixels is assigned a value illustrating one or more pressure regions corresponding to the impact on the body suit; and
generating an injury map using the pressure map and a machine learning model, wherein the machine learning model utilizes one or more input parameters specific to the user of the body suit to determine a neighborhood pressure expansion, wherein the neighborhood pressure expansion is utilized to expand the one or more pressure regions of the pressure map to one or more surrounding pixels based on the one or more input parameters specific to the user.

2. The method of claim 1, wherein the positional relationship between the user of the body suit and the single-track vehicle is determined based on a composite center of gravity, the composite center of gravity being a center of gravity relationship between the user of the body suit and the single-track vehicle.

3. The method of claim 1, wherein the machine learning model utilizes the one or more input parameters to determine a pressure mapping correlation, and wherein the pressure mapping correlation is a determined correlation between two or more body parts of the user based on the one or more input parameters, wherein the one or more input parameters include at least a medical history of the user of the body suit.

4. The method of claim 1, further comprising:
displaying, using the body suit, a criticality level of an injury utilizing one or more colors.

5. The method of claim 1, further comprising:
translating the injury map into one or more injury captions, wherein the one or more injury captions describe the injury map in words, and wherein the one or more injury captions are improved over time based on injuries resulting from the impact on the body suit being utilized as feedback for the machine learning model.

6. The method of claim 1, further comprising:
retraining the machine learning model using feedback received based on the accuracy of the injury map, wherein the machine learning model is a deep neural network which is trained based on the one or more input parameters specific to the user to determine the neighborhood pressure expansion, wherein the machine learning model is retrained to improve future injury maps and learn detailed injury descriptions.

7. The method of claim 1, further comprising:
retrieving, in response to a scanning of a portion of the body suit, the one or more input parameters specific to the user and additional information related to the impact on the body suit.

8. The method of claim 7, wherein the one or more input parameters and the additional information are displayed to a third party, wherein the additional information includes at least a velocity of the user of the body suit at a time of the impact and the time of impact.

9. The method of claim 1, wherein generating the pressure map further comprises:
determining the impact to the body suit using a voltage difference based on an electrical resistance variation utilizing a micro-controller to measure the electrical resistance as a function of time.

10. A computer system for impact response, comprising:
one or more processors, one or more computer-readable memories, one or more computer-readable tangible storage medium, and program instructions stored on at least one of the one or more tangible storage medium for execution by at least one of the one or more processors via at least one of the one or more memories, wherein execution of the program instructions causes the computer system to perform a method comprising:
triggering a stimulus if a threshold is reached or exceeded based on a positional relationship between a user of a body suit and a single-track vehicle, wherein the stimulus activates one or more pressure sensors integrated into a smart fabric of the body suit designed to measure an impact to the body suit;
generating a pressure map of the body suit utilizing the one or more pressure sensors, wherein the pressure map is comprised of a plurality of pixels corresponding to a plurality of intersection points of the smart fabric of the body suit, wherein each of the plurality of pixels is assigned a value illustrating one or more pressure regions corresponding to the impact on the body suit; and
generating an injury map using the pressure map and a machine learning model, wherein the machine learning model utilizes one or more input parameters specific to the user of the body suit to determine a neighborhood pressure expansion, wherein the neighborhood pressure expansion is utilized to expand the one or more pressure regions of the pressure map to one or more surrounding pixels based on the one or more input parameters specific to the user.

11. The computer system of claim 10, wherein the method further comprises determining the positional relationship between the user of the body suit and the single-track vehicle, wherein the positional relationship between the user of the body suit and the single-track vehicle is determined based on a composite center of gravity, the composite center of gravity being a center of gravity relationship between the user of the body suit and the single-track vehicle.

12. The computer system of claim 10, wherein the machine learning model utilizes the one or more input parameters to determine a pressure mapping correlation, and wherein the pressure mapping correlation is a determined correlation between two or more body parts of the user based on the one or more input parameters, wherein the one or more input parameters include at least a medical history of the user of the body suit.

13. The computer system of claim 10, wherein the method further comprises:
displaying, using the body suit, a criticality level of an injury utilizing one or more colors.

14. The computer system of claim 10, wherein the method further comprises:
translating the injury map into one or more injury captions, wherein the one or more injury captions describe the injury map in words, and wherein the one or more injury captions.

15. A computer program product for impact response, comprising:
one or more non-transitory computer-readable storage media and program instructions stored on at least one of the one or more tangible storage media, the program instructions executable by a processor to cause the processor to perform a method comprising:
triggering a stimulus if a threshold is reached or exceeded based on a positional relationship between a user of a body suit and a single-track vehicle, wherein the stimulus activates one or more pressure sensors integrated into a smart fabric of the body suit designed to measure an impact to the body suit;
generating a pressure map of the body suit utilizing the one or more pressure sensors, wherein the pressure map is comprised of a plurality of pixels corresponding to a plurality of intersection points of the smart fabric of the body suit, wherein each of the plurality of pixels is assigned a value illustrating one or more pressure regions corresponding to the impact on the body suit; and
generating an injury map using the pressure map and a machine learning model, wherein the machine learning model utilizes one or more input parameters specific to the user of the body suit to determine a neighborhood pressure expansion, wherein the neighborhood pressure expansion is utilized to expand the one or more pressure regions of the pressure map to one or more surrounding pixels based on the one or more input parameters specific to the user.

16. The computer program product of claim 15, wherein the method further comprises determining the positional relationship between the user of the body suit and the single-track vehicle, wherein the positional relationship between the user of the body suit and the single-track vehicle is determined based on a composite center of gravity, the composite center of gravity being a center of gravity relationship between the user of the body suit and the single-track vehicle.

17. The computer program product of claim 15, wherein the machine learning model utilizes the one or more input parameters to determine a pressure mapping correlation, and wherein the pressure mapping correlation is a determined correlation between two or more body parts of the user based on the one or more input parameters, wherein the one or more input parameters include at least a medical history of the user of the body suit.

18. The computer program product of claim 15, wherein the method further comprises:
   displaying, using the body suit, a criticality level of an injury utilizing one or more colors.

19. The computer program product of claim 15, wherein the method further comprises:
   translating the injury map into one or more injury captions, wherein the one or more injury captions describe the injury map in words, and wherein the one or more injury captions are improved over time based on injuries resulting from the impact on the body suit being utilized as feedback for the machine learning model.

* * * * *